United States Patent
Urick et al.

[19]

[11] Patent Number: 6,059,713
[45] Date of Patent: May 9, 2000

[54] CATHETER SYSTEM HAVING TUBULAR RADIATION SOURCE WITH MOVABLE GUIDE WIRE

[75] Inventors: Michael J. Urick, Rogers; Timothy G. J. Ehr, Elk River; Roger N. Hastings, Maple Grove, all of Minn.

[73] Assignee: SciMed Life Systems, Inc., Maple Grove, Minn.

[21] Appl. No.: 09/035,705

[22] Filed: Mar. 5, 1998

Related U.S. Application Data

[63] Continuation-in-part of application No. 08/984,490, Dec. 8, 1997, abandoned, which is a continuation-in-part of application No. 08/812,757, Mar. 6, 1997.

[51] Int. Cl.$^7$ ..................................................... A61N 5/00
[52] U.S. Cl. ................................................................. 600/3
[58] Field of Search ............................................. 600/1–8

[56] References Cited

U.S. PATENT DOCUMENTS

| | | | |
|---|---|---|---|
| 2,546,761 | 3/1951 | Loftus | 128/1.2 |
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parson, Jr. et al. | 250/497 |

(List continued on next page.)

FOREIGN PATENT DOCUMENTS

| | | |
|---|---|---|
| 2166915 | 8/1996 | Canada . |
| 0 433 011 B1 | 6/1991 | European Pat. Off. . |
| 0 497 495 A2 | 8/1992 | European Pat. Off. . |
| 0 514 913 A2 | 11/1992 | European Pat. Off. . |
| 0 593 136 A1 | 4/1994 | European Pat. Off. . |
| 0 633 041 A1 | 1/1995 | European Pat. Off. . |

(List continued on next page.)

OTHER PUBLICATIONS

Flexmedics, "Nitinol . . . The Material of Choice", 1989.
Sutherland, "Managing Cancer Through Synergy", *Administrative Radiology Journal*, Nov. 1996, pp. 21–27.
Raloff, "Nuclear Medicine Gets Friendlier—Experimental Therapies Seek to Poison Just the Disease", *Science News*, vol. 152, Jul. 19, 1997, pp. 40–41.

(List continued on next page.)

*Primary Examiner*—John P. Lacyk
*Attorney, Agent, or Firm*—Crompton, Seager & Tufte, LLC.

[57] ABSTRACT

A radiation source for inhibiting restenosis including a radiation delivery tube having a radioactive distal region, the tube being adapted to slide over a core wire within a radiation delivery catheter. The core wire is preferably in a slidable relation with the radiation delivery catheter. By withdrawing the core wire to a proximal position, the flexibility of a distal region of the radiation delivery catheter may be increased, thereby allowing the radiation delivery catheter to navigate more tortuous paths and reach more distal sites. Before the radiation delivery tube is advanced into the catheter distal region, the core wire is preferably slid distally to a distal position. With the core wire in the distal position, the core wire may provide a structure that can be used to rapidly advance the radiation source to the lesion site. The core wire may also help constrain lateral movement of the radiation delivery tube and help center the radiation delivery tube within the vessel to provide a more even radiation exposure to the vessel walls.

18 Claims, 7 Drawing Sheets

U.S. PATENT DOCUMENTS

| | | | |
|---|---|---|---|
| 4,244,357 | 1/1981 | Morrison | 128/1.2 |
| 4,281,252 | 7/1981 | Parson, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,799,479 | 1/1989 | Spears | 128/303.1 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,308,356 | 5/1994 | Blackshear, Jr. et al. | 606/194 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,417,653 | 5/1995 | Sahota et al. | 604/20 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,575,749 | 11/1996 | Liprie | 600/3 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |

FOREIGN PATENT DOCUMENTS

| | | |
|---|---|---|
| 0 686 342 A1 | 12/1995 | European Pat. Off. . |
| 0 688 580 A1 | 12/1995 | European Pat. Off. . |
| 0 696 906 B1 | 2/1996 | European Pat. Off. . |
| 0 749 764 A1 | 12/1996 | European Pat. Off. . |
| 0 754 472 A2 | 1/1997 | European Pat. Off. . |
| 0 754 473 A2 | 1/1997 | European Pat. Off. . |
| 0 778 051 A1 | 6/1997 | European Pat. Off. . |
| 0 801 961 A2 | 10/1997 | European Pat. Off. . |
| 0 813 894 A2 | 12/1997 | European Pat. Off. . |
| 0 629 380 B1 | 7/1998 | European Pat. Off. . |
| 91 02 312 U | 8/1992 | Germany . |
| 9102312 U | 8/1992 | Germany . |
| 195 26 680 A1 | 1/1997 | Germany . |
| 197 54 870 A1 | 8/1998 | Germany . |
| 197 24 233 C1 | 12/1998 | Germany . |
| WO 86/03124 | 6/1986 | WIPO . |
| WO 93/04735 | 3/1993 | WIPO . |
| WO 94/25106 | 11/1994 | WIPO . |
| WO 94/26205 | 11/1994 | WIPO . |
| WO 95/07732 | 3/1995 | WIPO . |
| WO 95/19807 | 7/1995 | WIPO . |
| WO 95/26681 | 10/1995 | WIPO . |
| WO 96/06654 | 3/1996 | WIPO . |

| | | |
|---|---|---|
| WO 96/10436 | 4/1996 | WIPO . |
| WO 96/13303 | 5/1996 | WIPO . |
| WO 96/14898 | 5/1996 | WIPO . |
| WO 96/17654 | 6/1996 | WIPO . |
| WO 96/22121 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/09937 | 3/1997 | WIPO . |
| WO 97/18012 | 5/1997 | WIPO . |
| WO 97/19706 | 6/1997 | WIPO . |
| WO 97/25102 | 7/1997 | WIPO . |
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36788 | 8/1998 | WIPO . |
| WO 98/36790 | 8/1998 | WIPO . |
| WO 98/36796 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 98/55179 | 12/1998 | WIPO . |
| WO 98/57706 | 12/1998 | WIPO . |
| WO 99/01179 | 1/1999 | WIPO . |
| WO 99/02219 | 1/1999 | WIPO . |
| WO 99/04706 | 2/1999 | WIPO . |
| WO 99/04856 | 2/1999 | WIPO . |
| WO 99/10045 | 3/1999 | WIPO . |

OTHER PUBLICATIONS

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No.1 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

Barry, "Reactive Oxygen Species in Living Systems—Source: Biochemistry, and Role in Human Disease", Internet Address http://www.livelinks.com/sumeria/oxy/reactive-.html, Jul. 21, 1997 from *American Journal of Medicine*, vol. 91, No. 3C, Sep. 30, 1991, p. 14S(9).

Block, "Peroxygen Compounds, Chapter 9", *Disinfection, Sterilization, and Perservation*, Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley, California, Dec. 1990.

Tjho–Heslinga et al., "Results of Ruthenium Irradiation of Uveal Melanoma", *Radiotherapty and Oncology*, vol. 29, 1993, pp. 33–38.

Lommatzsch et al., "Radiation Effects on the Optic Nerve Observed After Brachytherapy of Choroidal Melanomas with 106Ru/106Rh Plaques", *Graefe's Arch. Clin. Expo. Ophthalmol.*, 1994, 232:482–487.

Alberti, *Radiotherapy of Intraocular and Orbital Tumors*, Springer–Verlag, Berlin, Copyright 1993, pp. 363–367 and 23–30.

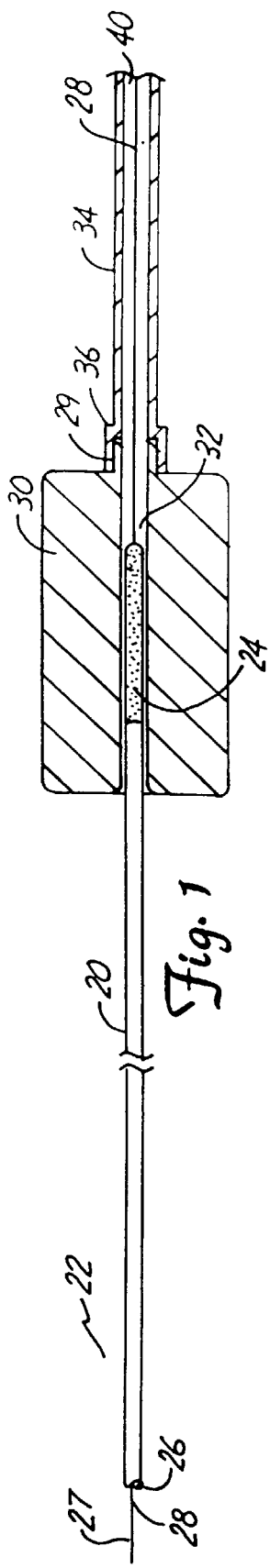
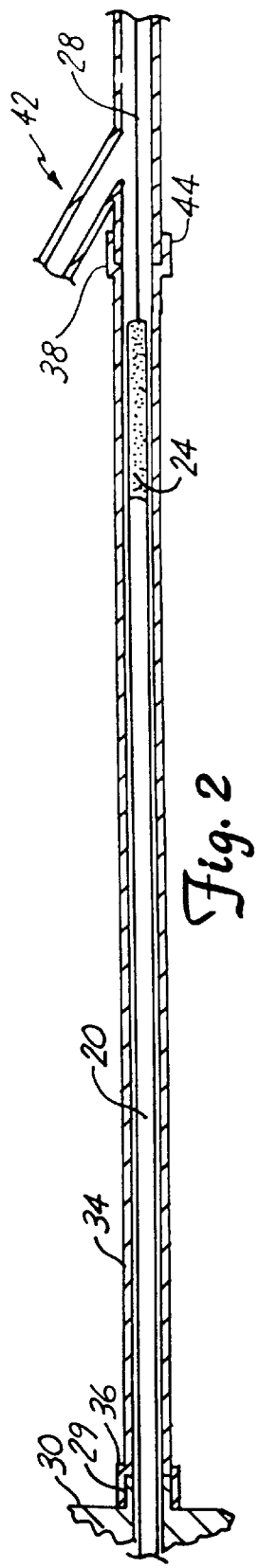
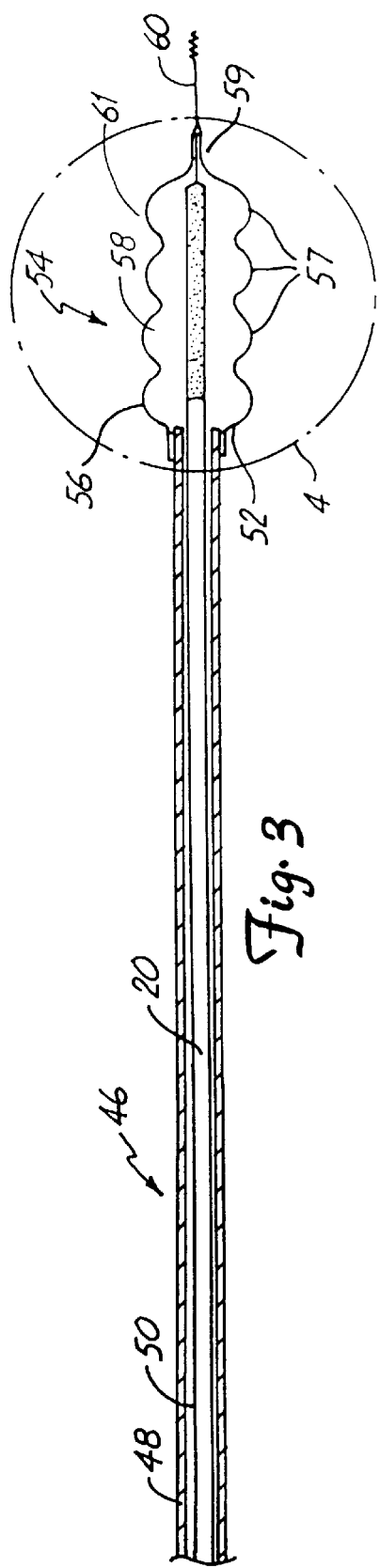

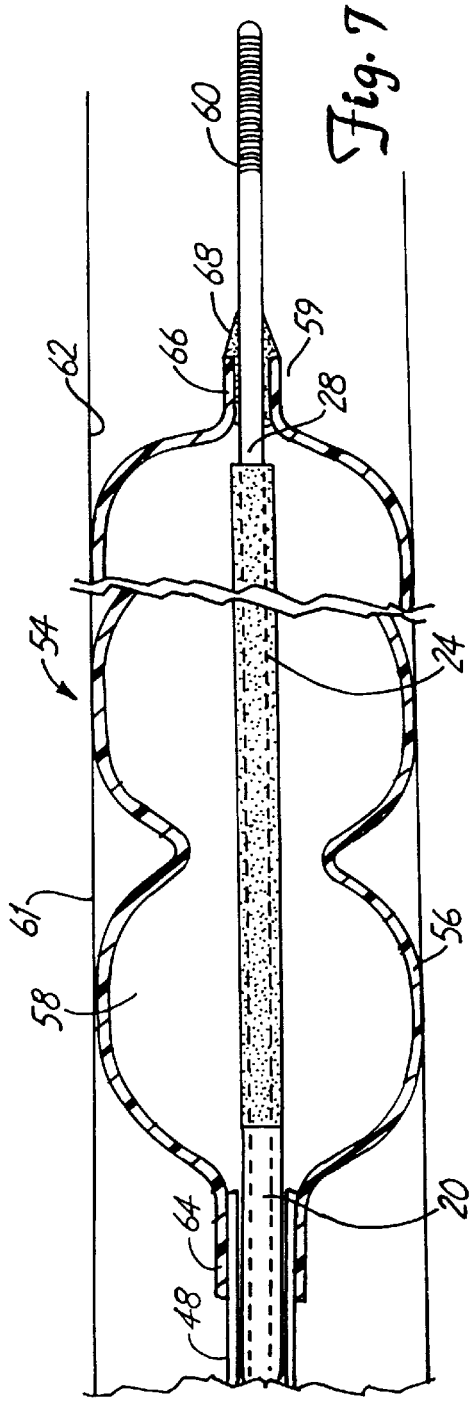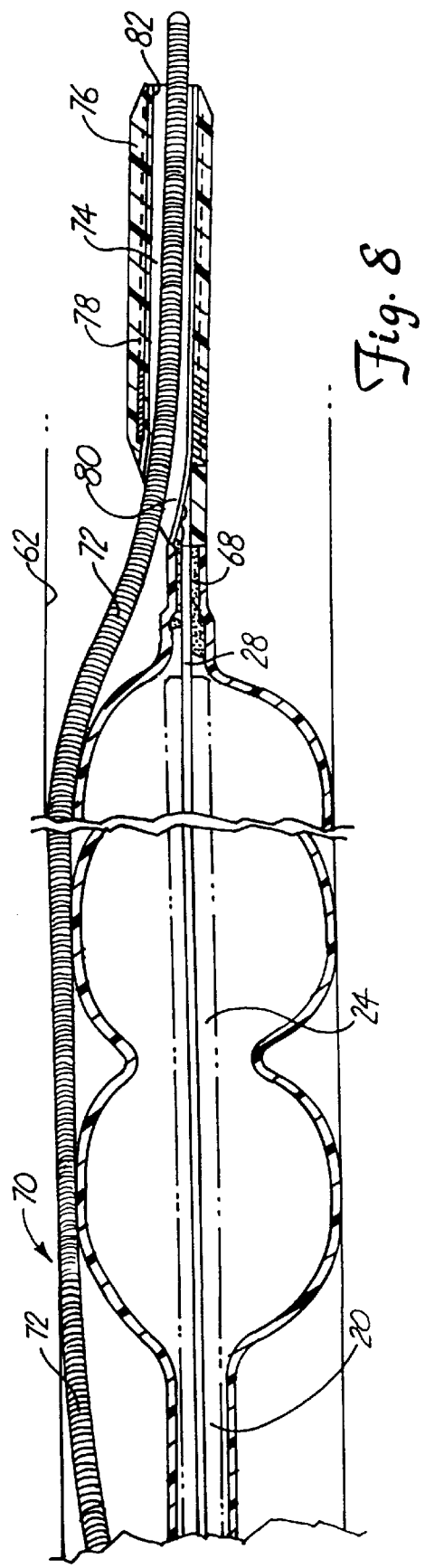

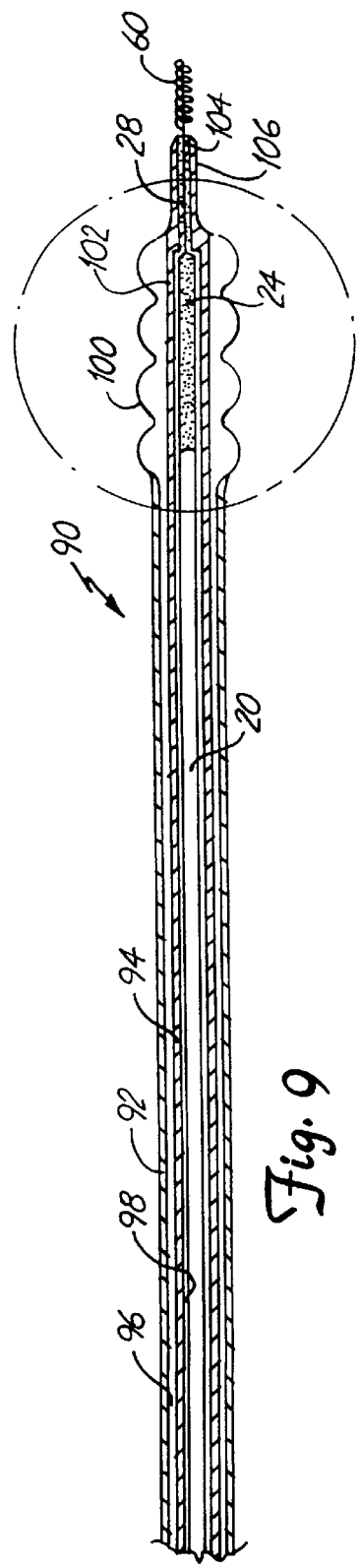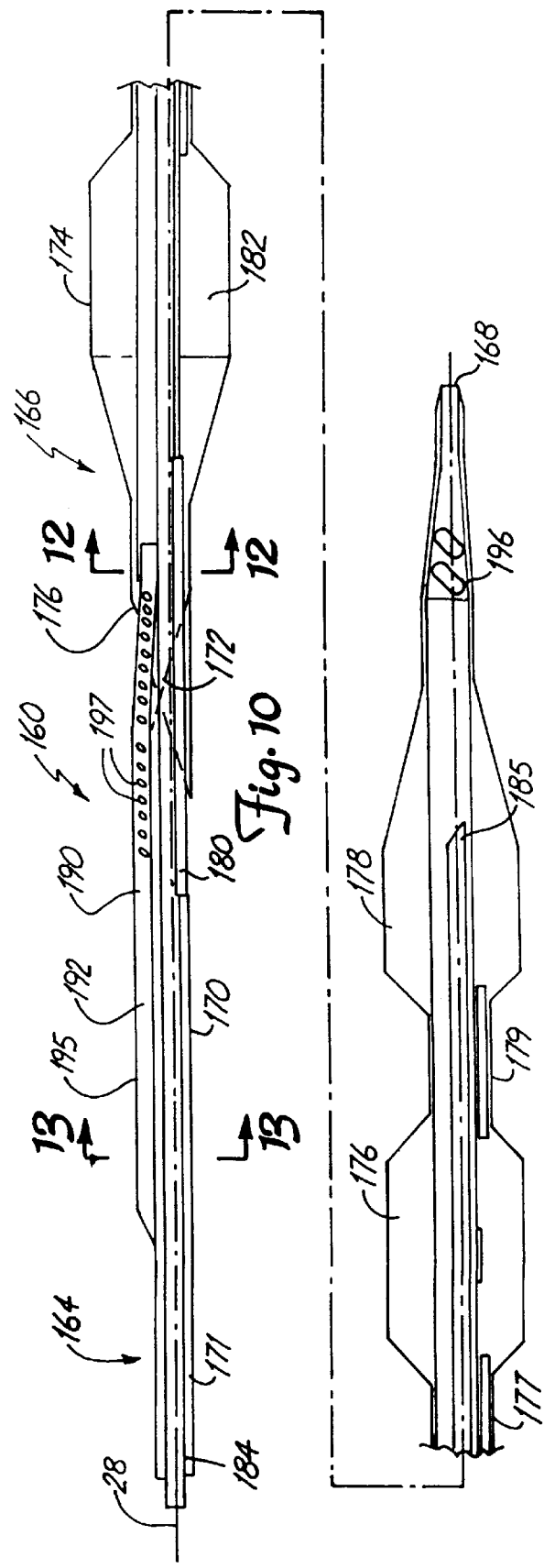

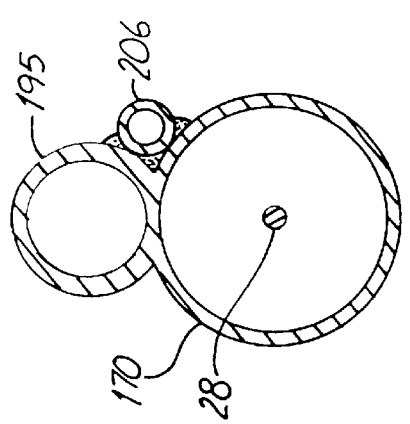
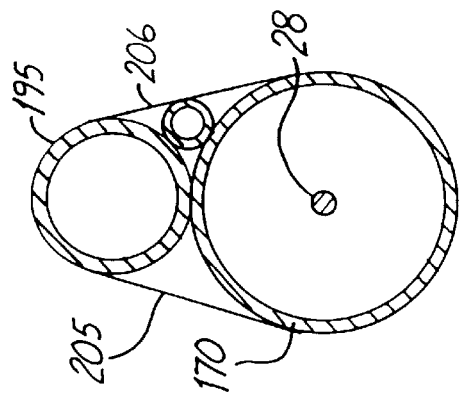
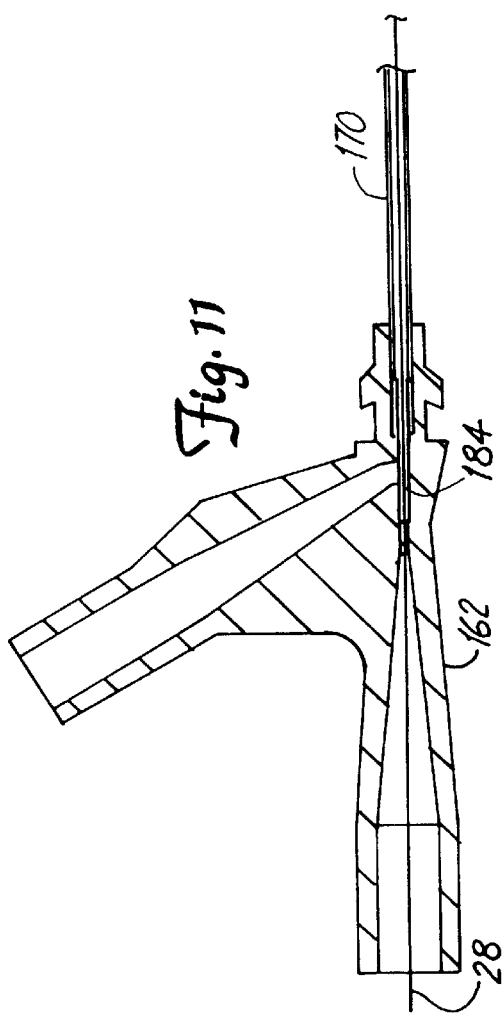
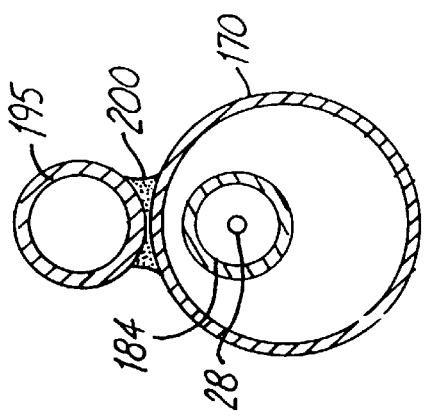
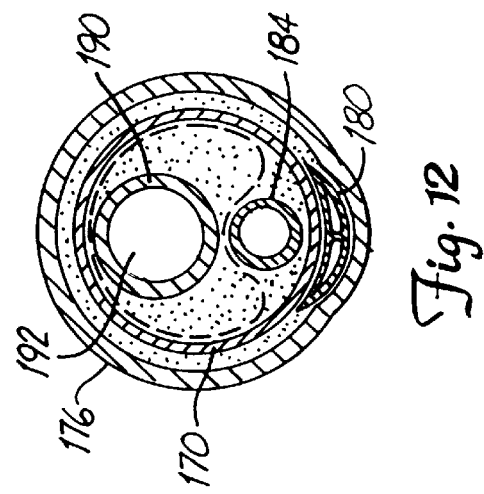

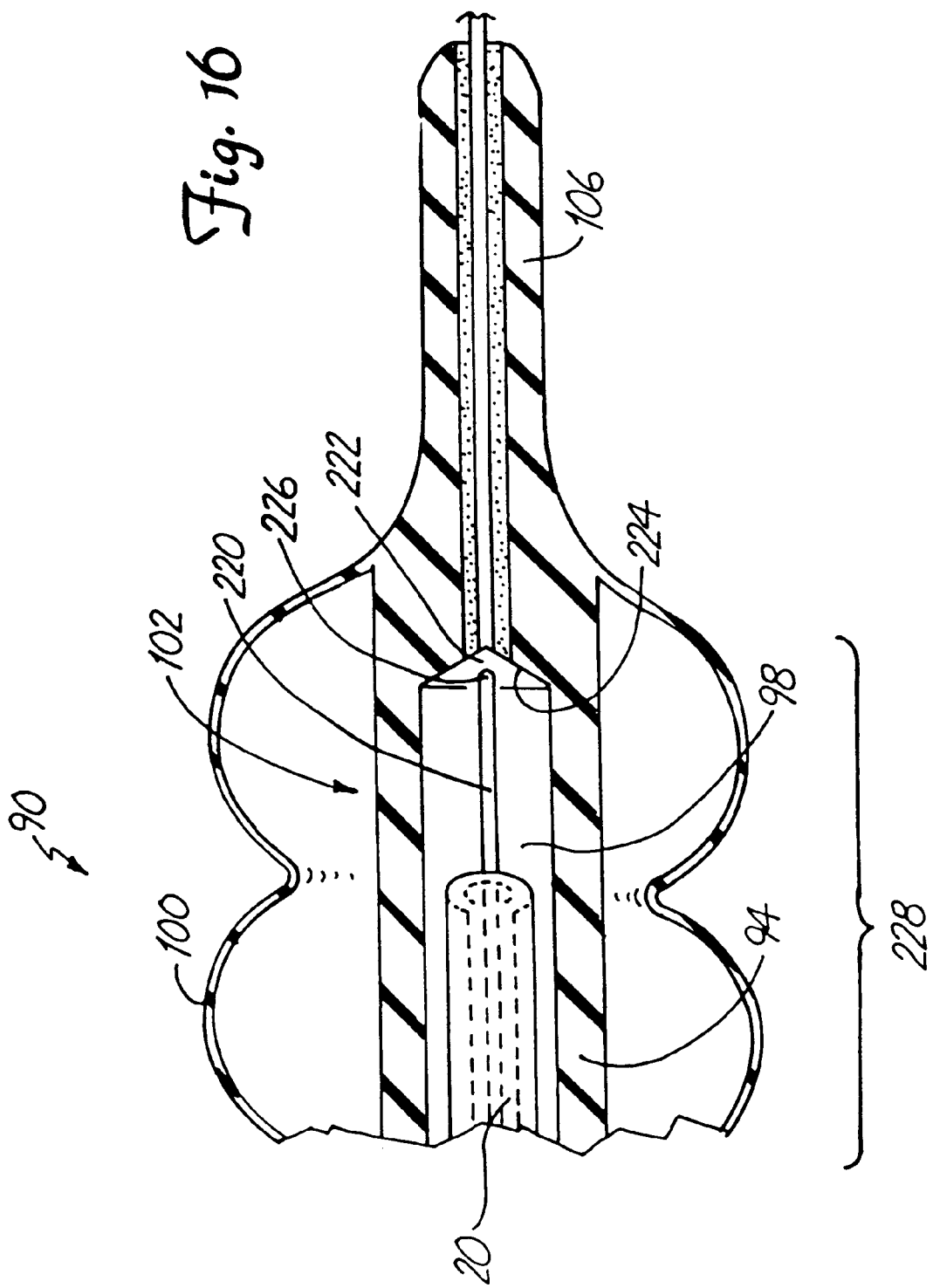

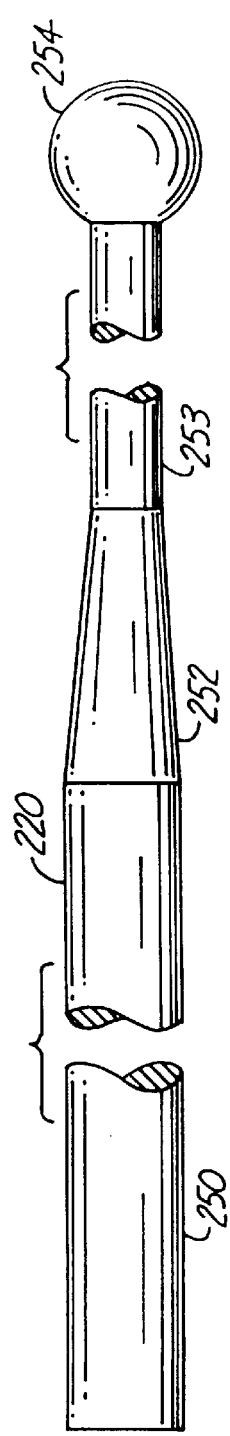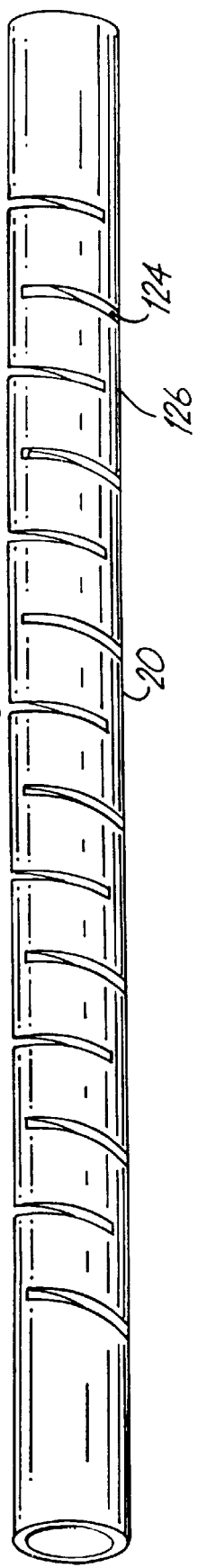

CATHETER SYSTEM HAVING TUBULAR RADIATION SOURCE WITH MOVABLE GUIDE WIRE

CROSS REFERENCES TO CO-PENDING APPLICATIONS

This application is a continuation-in-part of U.S. patent application Ser. No. 08/984,490, filed Dec. 8, 1997, entitled "Catheter System having Tubular Radiation Source", now abandoned; which is a continuation-in-part of co-pending U.S. patent application Ser. No. 08/812,757, filed Mar. 6, 1997, entitled "Perfusion Balloon Catheter with Radioactive Source", pending the entire disclosures of which are incorporated herein by reference. The present application is also related to co-pending U.S. patent application Ser. No. 08/782,471, filed Jan. 10, 1997, entitled "Intravascular Radiation Delivery System", pending; and to U.S. patent application Ser. No. 08/612,061, filed Mar. 7, 1996, entitled "Perfusion Balloon Angioplasty Catheter", now abandoned, the entire disclosures of which are herein incorporated by reference.

FIELD OF THE INVENTION

The present application is related to medical devices and methods for inhibiting restenosis in blood vessels. Specifically, the present invention is related to intravascular catheters utilizing a tubular member having a distally disposed radiation source over a core wire and methods of their use.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongate shaft with a balloon attached proximate to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of this restenosis is not fully understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. Delivery of radioactive radiation has been proposed as a means to prevent or reduce the effects of restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance for a point source and inversely with distance for a line, a source laying off center near one vessel wall may significantly overexpose the nearby wall while underexposing the further away wall. This is especially critical for beta radiation which is absorbed by tissue and blood at a relatively short distance from the source.

Use of continuous centering balloons having a beta radiation source within has been suggested, but may allow the radiation source to "warp" when placed across curved vessel regions, allowing the balloon to bend but having the central radiation source lying in a straight line between the two ends.

What remains to be provided is an improved apparatus and method for delivering uniform radiation to vessel interiors to inhibit restenosis.

SUMMARY OF THE INVENTION

The present invention includes a radiation source which can be used to inhibit restenosis of blood vessels, the source having a tubular radioactive distal region adapted to slide over a radiation source guide wire or core wire. In all embodiments, the radiation source guide wire or core wire extends within a lumen that extends over substantially the entire length of a delivery catheter. The core wire further extends out the proximal end of the delivery catheter a sufficient distance or length to thread the tube or radiation source thereon.

One radiation source includes a tubular body having a lumen the entire tube length, which can be used with a radiation source guide wire extending proximally out of the proximal end of a delivery catheter for at least the length of the tube to facilitate exchanges. Another source includes a tubular body having a lumen the entire tube length but having a first guide wire port on its distal end and a second guide wire exit port a short distance proximal of the distal end, allowing the use of a shorter radiation source guide wire extending proximally from the proximal end of the delivery catheter to thread the tube thereon.

Yet another source includes a short radioactive, tubular distal member disposed at the end of a shaft with the short distal tubular member having a distal and proximal opening for threading over the radiation source guide wire, again allowing the use of a radiation source guide wire which extends a short distance proximally out the proximal end of the delivery catheter to thread the tubular radiation source lumen thereon. The tubular body could also be of a two-piece construction with the short distal radiation portion detachable from a long proximal segment.

Still another radiation source features an elongate tubular body having a short distal radioactive portion and a lumen the entire tube length and having a longitudinal slot extending through the tube wall over a portion of the length of the tubular body. The slot extends from the proximal end of the tubular body, where it is open to the lumen at the proximal end, to a point proximate the radioactive portion. The slotted embodiment allows a radiation source guide wire to be threaded by extending the wire radially through the slot, holding the core wire position constant, while advancing the tube into the catheter and patient, thereby threading the entire tube while requiring the core wire to extend proximally from the proximal end of the delivery catheter a short distance about equal to the non-slotted length of the tubular body.

The tubular body can be formed of Nitinol. In a preferred embodiment, the elongate tubular body having the distally disposed radioactive source includes a plurality of cutouts or openings through the tubular wall in a distal portion thereof. The plurality of cutouts, holes or slots extend around the circumference of the tubular body and over a portion of the lengths thereof, wherein the cutouts are in a selected pattern separated by bridges of the material of the tubular body. The cutouts provide added flexibility in the distal portion of the tubular body which must navigate a more tortuous path to be positioned within the expandable balloon of the delivery catheter in a prior stenosed region. The cutouts, holes or slots may be distributed in any selected pattern to impart such increased flexibility. A preferred pattern includes a generally spiral or helical pattern of cutouts having bridges extending longitudinally between cutouts every 120 degrees. Alternatively, the distance between cutouts can vary over the length from 90 degrees to 240 degrees. Radiation sources according to the present invention can have radioactive material incorporated into the tubular material or secured to the surface of the tubular body. In preferred embodiments, the tubular member is made from Nitinol with a metallic radiation source plated onto a portion of the surface thereof.

The present invention includes an inflatable balloon delivery catheter having a closed end radiation delivery lumen and a radiation source guide wire or core wire within the lumen. The radiation source guide wire or core wire can be fixed relative to the radiation delivery lumen or slidably disposed within the radiation delivery lumen. In one catheter, the radiation delivery lumen can serve as the inflation lumen. Another catheter includes an inflation lumen separate from the radiation source delivery lumen. Another preferred embodiment of delivery catheter includes a separate radiation source lumen and a separate inflation lumen in combination with a single operator exchange guide wire lumen which doubles as a passive perfusion lumen during radiation treatment.

When the core wire is not fixed or otherwise attached to the distal end of the catheter, the core wire may be withdrawn to a proximal position or advanced to a distal position. In this configuration, the core wire may be withdrawn to the proximal position, preferably proximal of the balloon, to increase the flexibility of the distal region of the catheter. This may allow the distal region of the catheter to navigate more tortuous paths and reach more distal sites. Before the radiation delivery tube is advanced into the catheter distal region, the core wire is preferably moved distally to the distal position where the distal end abuts the closed end of the radiation delivery lumen. When the core wire is in the distal position, the radiation delivery lumen in combination with core wire may provide a structure that can be used to rapidly advance the radiation source to the lesion site. In addition, the core wire may help constrain lateral movement of the radiation delivery tube and help center the radiation delivery tube within the vessel, providing a more even radiation exposure to the vessel walls.

The tubular radiation source and delivery catheter can be used in conjunction with a radiation shield or vault and a transfer tube. The vault can shield the radiation source when the source is outside of the patient's body. The transfer tube can be used to quickly transfer the radiation source from the non-sterile vault into the sterile delivery catheter. A preferred vault includes a path with multiple bends to shield the entrance and exit of the vault.

The tubular shape of the radiation source can provide a more even radiation exposure to vessel walls. In particular, due to the relationship between distance and radiation intensity, the tubular shape reduces the amount of radiation or radioactivity need which reduces the cost of manufacturing and disposal.

BRIEF DESCRIPTION OF THE DRAWINGS

FIG. 1 is a fragmentary, longitudinal cross-sectional view of a radiation delivery tube having a radioactive distal region disposed over a radiation source guide wire and disposed within a radiation shielding vault coupled to a transfer tube;

FIG. 2 is a fragmentary, longitudinal cross-sectional view of the vault, transfer tube, radiation delivery tube, and radiation source guide wire of FIG. 1 coupled to a radiation delivery catheter proximal end;

FIG. 3 is a fragmentary, longitudinal cross-sectional view of a fixed wire radiation delivery balloon catheter having the radioactive region of the radiation delivery tube of FIG. 1 inserted within the balloon;

FIG. 7 is a fragmentary, longitudinal cross-sectional view of the balloon of FIG. 3;

FIG. 8 is a fragmentary, longitudinal view of the balloon portion of a single operator exchange catheter embodiment having a catheter guide wire disposed within a distal guide wire lumen;

FIG. 9 is a fragmentary, longitudinal cross-sectional view of a radiation delivery balloon catheter having a radiation delivery tube disposed within an inner tube which is in turn disposed within an outer inflation tube;

FIG. 10 is a fragmentary, longitudinal cross-sectional view of a delivery catheter incorporating a separate radiation delivery lumen, a separate inflation lumen and a combination perfusion lumen and single operator exchange guide wire lumen;

FIG. 11 is a fragmentary cross-sectional view of a manifold assembly for use in conjunction with the catheter of FIG. 10 depicting the core wire extending proximally from the proximal end of the manifold;

FIG. 12 is a cross section of the catheter of FIG. 10 at line 12—12;

FIG. 13 is a cross section of the proximal shaft portion of the catheter of FIG. 10 at line 13—13;

FIG. 14 is a cross section of an alternative proximal shaft portion similar to that of FIG. 13 incorporating a dual lumen extrusion for the proximal shaft;

FIG. 15 is a cross section of an alternative proximal shaft portion similar to FIG. 13 which depicts the use of multiple separate tubular shafts which are bundled to form the proximal shaft portion;

FIG. 16 is a fragmentary, partial longitudinal cross-sectional view of the distal end of a radiation delivery balloon catheter similar to that shown in FIG. 9, but with the radiation delivery core wire slidably disposed within the inner tube;

FIG. 17 is a partial perspective view of a preferred radiation delivery coil wire; and FIG. 18 is a partial perspective view of a preferred radiation delivery tube having a plurality of bridges and slots formed thereon.

DETAILED DESCRIPTION OF THE PREFERRED EMBODIMENTS

Figure 4:
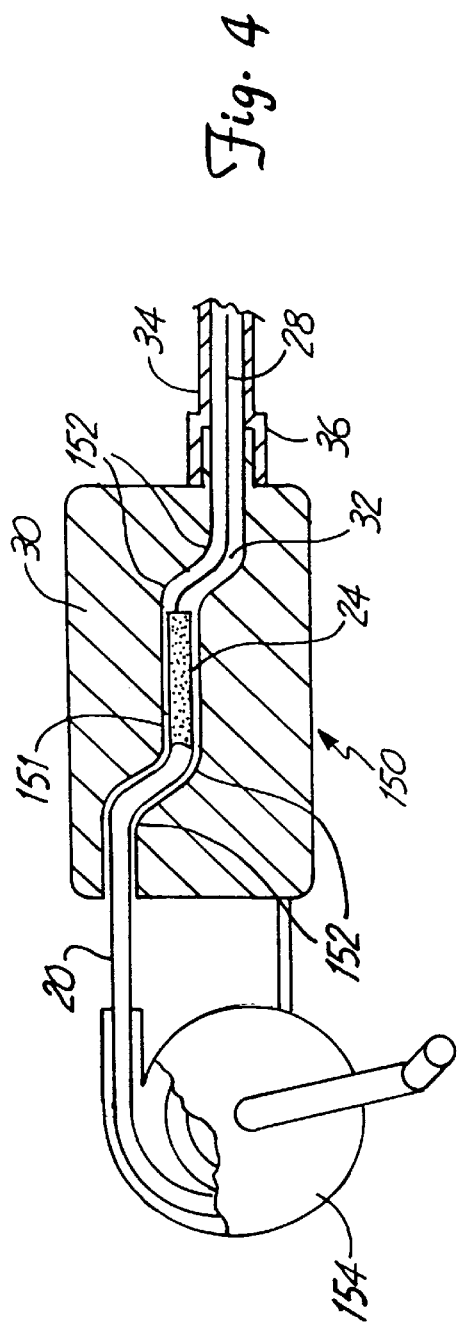
FIG. 4 is a schematic cross section of a preferred catheter management system including a vault having a tubular radiation source path therethrough including multiple bends to shield against radiation exposure in both a radial and longitudinal direction and a reel assembly which contains the non-radioactive portion of the tubular body.

Referring to FIGS. 1–3, an overall radiation delivery catheter system, including a radiation delivery tube 20, is schematically illustrated in various stages of deployment. FIG. 1 depicts the radiation delivery tube 20 as slidably mounted over a core wire or radiation source guide wire 28 while the distal portion or radioactive distal tubular region 24 remains shielded in a vault 30 prior to insertion into a catheter for use. FIG. 2 illustrates the radiation delivery tube 20 as extended distally from vault 30 into the lumen of a transfer tube 34, which in turn is connected to the proximal end 44 of a manifold 42 of a catheter 46. FIG. 3 depicts the radiation delivery tube 20 as fully extended distally into the catheter 46 with the distal radiation portion 24 of the radiation delivery tube 20 disposed within the balloon 56 for treatment of a stenotic region. It is noted that FIG. 3 depicts the catheter 46 as a fixed wire catheter having a single lumen. It is, however, recognized, as detailed herein, that the radiation delivery tube 20 of the present invention can be utilized in conjunction with other catheter designs which incorporate a lumen with a core wire extending therethrough and closed on the distal end to isolate the radiation delivery tube from the treatment site.

Now referring to FIG. 1 in more detail, FIG. 1 illustrates the radiation delivery tube or shaft 20 having a proximal region 22, a radioactive tubular distal region 24, and a lumen 26, disposed over a radiation source guide wire or core wire 28. In a preferred embodiment, proximal shaft region 22 has a lumen therethrough. In another embodiment, proximal shaft region 22 is solid, having no lumen. Radiation source guide wire 28 includes a proximal end 29, illustrated extending from radiation delivery tube proximal region 22. Radioactive distal region 24 is disposed within a channel 32 within a radiation shielding vault 30 coupled to a transfer tube 34. Transfer tube 34 includes a proximal coupling 36, a distal coupling 38 (illustrated in FIG. 2) and a lumen 40 therethrough. Radiation source guide wire 28 extends through radiation delivery tube 20, vault 30, and transfer tube 34. Radiation source guide wire 28 can originate distally in the distal end of a radiation delivery catheter 46 (illustrated in FIG. 3) and terminate in a proximal end 27.

A tubular member having a lumen extending through at least a distal portion thereof and a radiation source disposed on or in a distal segment thereof is the preferred device for delivery of radiation according to the present invention. Specifically, a tubular shaped source is preferred relative to a point or line source. The intensity of radiation delivered drops off exponentially with the distance between the radiation source and target, and is particularly affected by absorption in blood and tissue. A tubular source has radiation emitted from the tube walls surrounding the central axis of the tube, the radiation sources being disposed much closer to the target than would be sources positioned along the center of the tube. The tube shape is similarly shaped to most vessels being treated. The use of tubular sources allows advancing radiation sources over wires within existing catheters, not absolutely requiring the use of specialized devices to support delivery of a radiation source. As the radioactive material can be closer to the targeted vessel walls than the corresponding point or line source, the local strength of the sources can be less. This means less radioactivity is necessary and the cost of manufacturing and disposal is reduced. In one embodiment, tube 20 has an inside diameter of about 0.014 inches to about 0.018 inches and an outside diameter of about 0.0175 inches to about 0.022 inches.

A preferred diameter for radiation source guide wire or core wire 28 is about 0.012 inch. Radiation source guide wire 28 can be formed from materials well known to those skilled in the art, such as stainless steel or Nitinol. In all embodiments of the invention illustrated, radiation source guide wire 28 is used to guide a radiation source slidably disposed thereover. Preferably, radiation source guide wire 28 terminates in the catheter distal region, and is contained in a lumen such that radiation delivery tube 20 is not in contact with bodily fluids. Contamination of the radiation source by bodily fluids is thus avoided. This allows for re-use of the radiation source in multiple patients.

Radiation delivery tube 20 can be formed from polymeric or metallic materials. Suitable polymers can include polyesters, polyamide or polyether block amides (PEBA). Suitable metals include stainless steel and Nitinol. Radiation delivery tube lumen 26 extends through the entire tube length in some embodiments. In other embodiments, tube 20 has a short lumen extending only through a distal tube region, having a proximal port in the distal region. This port allows radiation source guide wire proximal end 27 to be threaded through the short lumen portion, not requiring a radiation source guide wire extending proximally out of the proximal end of the delivery catheter at least a distance equal to the length of the radiation delivery tube. In embodiments having a lumen extending the entire length of tube 20, the radiation source wire must extend for at least this length from the proximal end of the catheter to allow for threading of the lumen without losing control of the wire.

Figure 5:
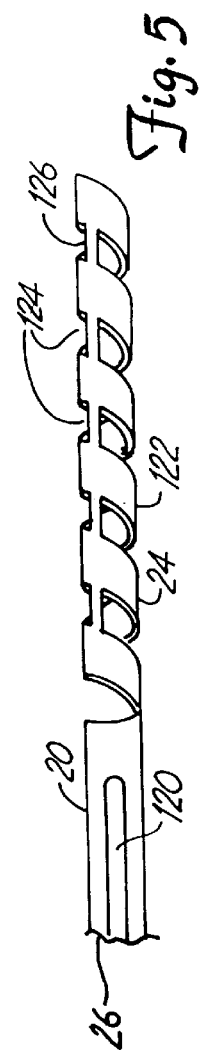
FIG. 5 is a plan view of a preferred radioactive tubular body construction incorporating a guide wire slot extending from the proximal end of the tubular body to a point proximate the radioactive portion of the tubular body and also incorporating a plurality of cutouts to increase flexibility of the distal portion of the tubular body.

As depicted in FIG. 5, radiation delivery tube 20 can include a longitudinally extending slot 120 which extends from the proximal end of the radiation delivery tube 20 to a point proximate the radioactive tubular distal region 24. This "slotted tube" embodiment radiation delivery tube 20 has a lumen 26 extending the entire length of the tube 20 and a slot 120 through the tube wall into the lumen extending from the proximal end of the radiation delivery tube to a point proximate the distal portion of the radiation tube 20, with a short distal segment remaining unslotted. In this embodiment, the radiation source guide wire can be threaded through the lumen 26 of the short unslotted segment, extending transversely through the distal most portion of the slot. As the radiation delivery tube is advanced distally, the radiation source guide wire or core wire fits radially through the slot into the lumen causing the entire wire to ultimately lie within the lumen when the delivery tube is fully advanced. In yet another embodiment, radiation delivery tube 20 includes a solid proximal radiation delivery shaft, with only the distal region having a lumen with proximal and distal openings to accept a wire.

As previously stated, the radiation delivery tube 20 can preferably be formed of Nitinol. As depicted in FIG. 5, the distal portion 122 of the radiation delivery tube 20 preferably includes a plurality of cutouts or openings 124 through the tubular wall in that distal portion. The plurality of cutouts, holes or slots extend around the circumference or a portion of the circumference of the radiation delivery tube in spaced arrangement over a portion of the length thereof. The cutouts are in a selected pattern separated by bridges 126 of the Nitinol material of the tubular member. These cutouts 124, in conjunction with the bridges 126, provide added flexibility in the distal portion of the radiation delivery tube 20. This assists in allowing the radiation delivery tube 20 to navigate the more tortuous path to the stenosed region. Although it is recognized that many patterns of cutouts, holes or slots may be utilized to impart the increased flexibility, a preferred pattern includes a generally spiral or helical pattern of cutouts having bridges extending longitudinally between cutouts every 120 degrees.

Referring now to FIG. 18, a preferred radiation delivery tube 20 is depicted. As with the embodiment of FIG. 5, the plurality of slots 124 extend around the circumference or a portion of the circumference of the radiation delivery tube in spaced arrangement over a portion of the length thereof. The cutouts are in a selected pattern separated by bridges 126. In the preferred embodiment of FIG. 18, the slots and bridges extend over a portion of the distal-most portion of the radiation delivery tube 20. Preferably, these slots and bridges extend over the distal-most 2 to 4 inches of the radiation delivery tube 20. Preferably, the slots extend over approximately the last 3 inches and terminate about 0.030 inches from the distal end of the radiation delivery tube 20. These slots and bridges over this distal portion of the radiation delivery tube are specifically designed to improve pushability, pullability and to add some torqueability to the radiation delivery tube 20. Further, these slots and bridges are designed to give increasing flexibility to the radiation delivery tube 20 from the proximal-most slot to the distal-most slot by decreasing the frequency of bridges thereon. In a preferred embodiment, the slots are spaced axially over the length of the catheter at a spacing of about 0.01 to about 0.02 inches with a preferably space between slots of about 0.012 inches. Further, the bridges begin at the proximal portion of the slotted portion of the radiation delivery tube at a frequency of one bridge every 90° with a 15° increase every full turn around the tube. When the bridges are 240° apart, the spacing of the bridges around the outside of the radiation delivery tube 20 are maintained constant to the distal end. The table below indicates the bridge locations based on the above-described preferred design. The bridge location data begins with 0 at the proximal-most portion of the first slot and continues increasing with distance traveled around the tubular member with 360 constituting a complete revolution. The angle between bridges is that distance between bridges defined in the angle traveled from one bridge to the next bridge around the tubular member. The revolutions around the shaft define the bridge locations beginning at 0 where the first slot beings on the proximal-most portion of the shaft and increases based on cumulative revolutions from that point.

TABLE 1

| Bridge Location | Angle Between Bridge | Revolutions Around Shaft |
| --- | --- | --- |
| 0 | 0 | |
| 90 | 90 | 0.25 |
| 180 | 90 | 0.5 |
| 270 | 90 | 0.75 |
| 360 | 90 | 1.0 |

TABLE 1-continued

| Bridge Location | Angle Between Bridge | Revolutions Around Shaft |
| --- | --- | --- |
| 450 | 105 | 1.25 |
| 555 | 105 | 1.54166667 |
| 660 | 105 | 1.83333333 |
| 765 | 105 | 2.125 |
| 870 | 120 | 2.41666667 |
| 990 | 120 | 2.75 |
| 1110 | 120 | 3.08333333 |
| 1230 | 135 | 3.41666667 |
| 1365 | 135 | 3.79166667 |
| 1500 | 135 | 4.16666667 |
| 1635 | 150 | 4.54166667 |
| 1785 | 150 | 4.95833333 |
| 1935 | 165 | 5.375 |
| 2100 | 165 | 5.83333333 |
| 2265 | 180 | 6.29166667 |
| 2445 | 180 | 6.79166667 |
| 2625 | 195 | 7.29166667 |
| 2820 | 195 | 7.83333333 |
| 3015 | 210 | 8.375 |
| 3225 | 210 | 8.95833333 |
| 3435 | 225 | 9.54166667 |
| 3660 | 225 | 10.1666667 |
| 3885 | 240 | 10.7916667 |

Figure 6:
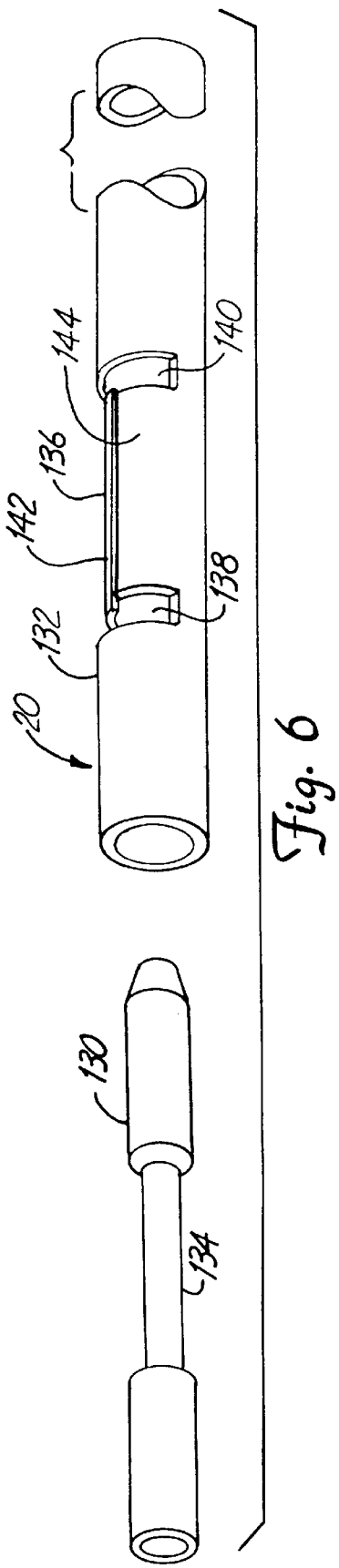
FIG. 6 schematically depicts a two-piece tubular radiation source which includes a detachable distal portion having the radioactive source thereon and a long proximal member for attachment thereto.

Referring now to FIG. 6, an alternative two-piece embodiment of radiation delivery tube 20 is depicted. The two-piece embodiment includes a proximal member 130, which is releasable securable to a distal member 132. When attached together, the two members 130, 132 form the complete tubular radiation source 20, which can be utilized as previously described. In one preferred embodiment, as depicted in FIG. 6, the proximal member 130 includes a portion of reduced outside diameter 134. The distal member 132 includes a region 136, having a reduced diameter lumen. The reduced diameter lumen 136 illustrated in FIG. 6 is formed by cutting partial radial slots 138, 140 in spaced relation about equal to the length of the reduced diameter portion 134 of the proximal member 130. A slot 142 is cut longitudinally between the radial slots 138, 140. This forms two wings 144 from the wall material, which may be bent inwardly toward the center of the lumen, to form a portion of reduced diameter in the lumen. In this way, the reduced diameter portion 134 of proximal member 130 can be snap fit into the reduced lumen diameter portion of the distal member 132. The two-piece tubular member 20 design can be particularly useful with the radiation source disposed only on the distal member 132. In this way, the radiation containing member can be stored or shielded separately from the overall device.

As previously discussed with respect to FIG. 1, the radioactive portion of the radiation of the tube 20 is stored within a vault 30 prior to actual use in order to shield personnel from exposure. FIG. 4 illustrates a preferred design for a radiation tube 20 storage and handling device 150. First, the vault assembly 30 includes a lumen 32 which extends through the vault having a path which incorporates multiple bends or offsets 152. As depicted, the multiple bends or offsets provide shielding for personnel both in the radial and longitudinal directions when the radioactive distal portion 24 is disposed within the central cavity 151 of the vault 30. As also depicted in FIG. 4, the storage and delivery system can include a reel assembly 154 which is fixedly secured to the vault 30 proximal thereof. The reel assembly 154 can be utilized to manage the proximal or non-radioactive portion of the tubular radiation source 20. It can thus be used for storage, but also for advancing and retracting the tubular radiation source 20. Thus, the overall unit can be utilized to transfer or transport the assembly while always maintaining the radioactive distal portion 24 within the central cavity 151.

A preferred source of radiation to be used with the present invention is a ruthenium/rhenium source, in particular $Ru/Rh_{106}$. This source is particularly useful in conjunction with a Nitinol radiation delivery tube as it can be plated onto the exterior surface of a distal portion of the radiation tube 20. This source decays with a half-life of 1.02 years, with low energy beta emissions and minor gamma emissions to $Rhodium_{106}$. $Rhodium_{106}$ emits high energy beta radiation with a half life of 29.8 seconds and decays into stable $Palladuim_{106}$. An alternative source of radiation for all embodiments of the present invention is the radioactive compound Nickel-66. Nickel-66 decays with a half life of 2.28 days with only low energy beta emissions and no gamma emission into its daughter element Copper-66. Copper-66 then emits high energy beta radiation with a half life of 5.10 minutes and decays into the stabile element Zinc-66. This two-step decay has a particular advantage in use in the catheters of the present invention.

The Nickel-66 acts as a carrier for the high energy copper decay allowing for time to transport the source to the end user, and also allows for disposal of the device through ordinary means in about 23 days. A Copper-66 source alone would decay quickly and not be useful without the parent Nickel. Nickel is low cost and has desirable mechanical properties in its pure form and in alloys, such as a Nickel Titanium alloy.

Another preferred radiation source is Gadolinium-153. Gadolinium-153 is a composite gamma source which can provide low energy gammas to vessel intima layer while providing higher energy gammas to penetrate calcified plaques and reach the adventitia. Moderate shielding can be used with Gadolinium-153, allowing the treating physician to remain in the room with the patient during therapy. Another preferred source of radiation can include Yttrium-90, a high energy beta emitter.

The above mentioned sources and other sources could be incorporated into the radiation delivery tube. In one embodiment, radioactive materials are admixed with polymeric materials and extruded as part of the tube. In another embodiment, radioactive materials are adhesively secured to the tube distal region. In yet another embodiment, radioactive material is included in wire form and wound around the tube distal region. The length of the tube radioactive distal region can be sized to approximate the length of the stenosis to be treated.

Referring again to FIG. 2, distal coupling 29 on vault 30 is mated to proximal coupling 36 on transfer tube 34, and a distal coupling 38 on transfer tube 34 is mated to a proximal end 44 of a radiation delivery catheter 42. Radiation source guide wire 28 is illustrated extending from catheter 42. Transfer tube 34 serves to transfer radioactive tube region 24 from vault 30 into catheter 42. Transfer tube 34 can reduce the chance of damage to radiation delivery tube distal end 24 caused by entering catheter proximal end 44 while off-center.

Referring again to FIG. 3, a fixed wire radiation delivery balloon catheter 46 is illustrated, having a tubular shaft 48 defining a lumen 50 within. Catheter 46 includes a distal region 52 and a distally disposed inflatable centering balloon 54. Balloon 54 includes a balloon envelope 56 which defines generally a balloon interior 58 and an exterior 61. Catheter 46 terminates in a distal end 59 which is sealed to prevent entry of bodily fluids into catheter lumen 50 and exit of inflation fluid from lumen 50. Balloon interior 58 is thus not in fluid communication with balloon exterior 61. In a preferred embodiment, a distal coil 60 forms the distal most portion of catheter 46.

In a preferred embodiment, balloon 54 is a multi-waisted centering balloon having a plurality of lobes or segments 57 as illustrated in FIG. 3. Balloon segments 57 in one embodiment are formed from a series of balloon tubes adhesively secured together. In another embodiment, balloon segments 57 are formed by blow molding. In this embodiment, balloon segments 57 can be spaced about 2 to 5 millimeters apart. In yet another embodiment, balloon segments are formed by spirally winding at least one inflatable tube about the catheter longitudinal axis.

Balloon 54 is preferably multi-waisted to provide improved centering capabilities. When a balloon carrying a tube within lies in a curved vessel passage, the balloon may have an arcuate shape conforming to the vessel, while the tube lies along a straight line joining the balloon ends. The straight line shape can bring the tube into very close proximity to the inside wall of the vessel curve. This can result in radiation overexposure and underexposure for the inside and outside walls of the curve, respectively. Use of a multi-waisted balloon can force the radiation tube inside to conform to an arcuate shape through the balloon waist centers.

Referring now to FIG. 7, balloon 54 is illustrated in more detail, disposed within vessel walls 62. Balloon envelope 56 includes a proximal waist 64 secured to tubular shaft 48 and a distal waist 66 secured over core wire 28. In one embodiment, balloon waists 64 and 66 are secured with adhesive or solvent bonding to underlying tube 48 and core wire 28, respectively. Radiation source guide wire 28 is secured to balloon distal end 59 in a fluid tight manner, such that distal fluid transfer in or out of balloon 54 is prevented. Radiation source guide wire 28 is fixed within balloon 54, such that wire 28 is not slidable relative to balloon 54. The annular space in lumen 50 between radiation source guide wire 28 and tubular shaft 48 defines an inflation lumen for inflating balloon envelope 56.

Referring now to FIG. 8, a single operator exchange radiation delivery catheter 70 is illustrated, having a catheter guide wire 72 disposed within a distal guide wire lumen 74. Radiation delivery catheter 70 is similar in many respects to fixed wire catheter 46, but having the ability to track over a guide wire. Catheter 70 includes a distal guide wire tube 76 having guide wire lumen 74, a proximal port 80, and a distal port 82. In a preferred embodiment, distal guide wire tube 76 includes a ribbon coil 78 embedded within to impart spring-like flexibility characteristics to the catheter distal tip. Coil 78 allows distal tube 76 to bend around tortuous curves without kinking yet return to a substantially straight tubular shape in straight passages.

Referring now to FIG. 9, a dual lumen embodiment of the present invention is illustrated in a catheter 90 having an outer tube 92 disposed about an inner tube 94. An inflation lumen 96 is defined in the annular space between outer tube 92 and inner tube 94. A radiation delivery lumen 98 is defined within inner tube 94 and is illustrated having radiation delivery tube 20 disposed within. Inflation lumen 96 is in fluid communication with an inflatable balloon 100. Inner tube 94 includes a distal region 102 extending through balloon 100 and sealing the interior of balloon 100 from radiation delivery lumen 98. In the embodiment illustrated, radiation source guide wire 28 is sealed with an adhesive 104 within a distal end 106 of catheter 90, terminating in distal coil 60.

In dual lumen catheter 90, radiation delivery tube 20 can remain dry during the procedure and no seal is required around the radiation source guide wire prior to inflation. In one embodiment, outer tube 92 has an outside diameter of about 0.045 inch and an inside diameter of about 0.040 inch. In one embodiment, inner tube 94 has an outside diameter of about 0.034 inch and an inside diameter of about 0.028 inch.

In use, a catheter such as catheters 42 and 46 illustrated in FIGS. 2 and 3 can be provided and inserted into a patient. Catheter 46 can be advanced until balloon 54 is in position across a treatment site having a lesion to be irradiated, leaving the catheter proximal end extending from the patient. A radiation delivery tube such as tube 20 of FIG. 1 can be provided, having radioactive distal region 24 shielded within vault 30. Transfer tube 34 can optionally be provided, interposed between, and coupled to, vault distal coupling 29 and catheter proximal end 44. Balloon 54 can be inflated with inflation fluid, dilating the stenosed vessel region. Radiation delivery tube radioactive region 24 can be rapidly advanced through transfer tube 34 and catheter lumen 50 to catheter distal region 52. After exposing the vessel treatment site for an appropriate period, radiation delivery tube 20 can be withdrawn into vault 30.

In embodiments having a common inflation and radiation delivery lumen, a seal can be provided around the radiation source guide wire near the proximal end of the catheter, to seal in inflation fluid. In embodiments having a separate inflation lumen, a seal is not required to contain inflation fluid and the radiation delivery tube can remain dry the entire procedure.

Referring now to FIG. 10, a preferred single operator exchange catheter design including a passive blood perfusion lumen and a radiation delivery tube lumen is illustrated. The figure shows a distal portion of catheter 160 connected proximally to a manifold 162 (the manifold is depicted in FIG. 11), having a proximal region 164, a distal region 166, and a distal end 168. The proximal region 164 of the catheter depicted in FIG. 10 includes a proximal shaft 170 which extends distally to a skived terminal end 172 which is proximal of the proximal balloon 174.

The proximal shaft portion 170 and skived portion 172 are affixed to a distal shaft portion 176 at the juncture as depicted. With the termination of the proximal tube 170, an inflation tubular member 180 extends from the distal end thereof and is in fluid communication with the lumen of the proximal tube 170. The distal end of the inflation tube 180 extends into the interior volume 182 of the balloon 174. Thus, inflation fluid may be transferred via the lumen 171 of proximal tube 170 into the balloon 174 through inflation tube 180. As depicted in FIG. 10, the balloon catheter of the present invention preferably includes multiple balloons to form multiple expandable segments. FIG. 10 depicts a proximal balloon 174, an intermediate balloon 176 and a distal balloon 178. Communication between the three balloons for inflation fluid is provided by an intermediate balloon inflation tube 177 and a distal balloon inflation tube 179 as depicted in FIG. 10. Alternatively, the inflation tubular member 180 can extend into all three balloons with an opening to the interior of each.

Also depicted in FIG. 10 is an inner tubular member 184 which extends from the proximal end of the catheter across the juncture between the proximal shaft 170 and distal shaft 176 into the interior of the balloon and terminates at a distal end 185 proximate the distal end of the distal balloon 178. This inner tubular member has a lumen extending therethrough which is closed at the distal end 185. The lumen has a core wire 28 extending therein. This lumen provides the conduit for insertion of and tracking of a radiation delivery tube 20 (not shown) as previously discussed herein.

Referring now also to FIG. 12, a cross-sectional view of catheter 160 at line 12—12, including distal region 166 is shown in more detail. Proximal shaft 170 is joined to distal shaft 176 with a crimped tube distal end 172. A guide wire tube 190 including a guide wire lumen 192, extends distally through the catheter, exiting catheter 160 at a distal port 168. Guide wire tube 190 extends through the balloons and is formed by distal shaft 176. A guide wire lumen proximal extension 195 extends proximally from distal shaft 176 along the exterior of proximal shaft 170. The catheter 160 includes proximal perfusion ports 197 through the wall of guide wire lumen proximal extension 195 and distal perfusion ports 196. Thus, during treatment, a guide wire extending through the guide wire lumen can be pulled back proximally to a point proximal of the proximal perfusion ports 197. This provides a perfusion pathway between the proximal ports 197 and distal ports 196, and accompanying blood flow during prolonged treatment.

FIG. 13 depicts a cross section of the catheter in FIG. 10 at line 13—13. The proximal guide wire extension 195 is depicted affixed to the outside diameter of proximal tube 170 via an adhesive bond 200. FIG. 13 also depicts core wire 28 extending within the inner tube 184.

FIGS. 14 and 15 depict alternative designs for the proximal portion of the catheter 160 with FIG. 14 incorporating a dual lumen proximal tubular member 170, and the catheter of FIG. 15 incorporating multiple tubular members in side-to-side relation bundled in a shrink wrap 205. The cross sections of FIGS. 14 and 15 are taken at line 13—13 of FIG. 10. The core wire 28 is depicted in both alternative embodiments within proximal tubular member 170. A separate inflation tubular member 206, having a lumen therethrough extends exterior to the proximal tubular member 170. The proximal guide wire extension 195 is an integral part of proximal tubular member 170 in FIG. 14, while in FIG. 15, the extension 195 is held to the exterior surface of the proximal tube 170 via the shrink wrap 205.

FIG. 16 shows the distal portion of a radiation delivery balloon catheter similar to that shown and described with reference to FIG. 9, but with the core wire 220 shown in a slidable relationship with inner tube 94. As in FIG. 9, an inflation lumen (not shown) is defined in the annular space between outer tube 92 and inner tube 94. A radiation delivery lumen 98 is defined within inner tube 94 and is illustrated having radiation delivery tube 20 disposed within. Inflation lumen 96 (see FIG. 9) is in fluid communication with an inflatable balloon 100. Inner tube 94 includes a distal region 102 extending through balloon 100 and sealing the interior of balloon 100 from radiation delivery lumen 98.

Unlike the embodiment shown in FIG. 9, however, the core wire 220 is not fixed or otherwise attached to the distal end 106 of catheter 90. Rather, the core wire 220 can slide longitudinally relative to inner tube 94. Accordingly, the core wire 220 may be withdrawn to a proximal position or advanced to a distal position, relative to the distal end 222 of the radiation delivery lumen 98.

Preferably, a centering cone 224 is positioned at or near the distal end of the radiation delivery lumen 98. The centering cone 224 is adapted to receive and help center the distal end 226 of the core wire 220 when advanced to the distal position. A distal coil 60 (see FIG. 9) may be attached to the distal end 106 of inner tube 94, and extend distally therefrom.

In use, the core wire 220 may be withdrawn to the proximal position, preferably proximal of the balloon 100, to increase the flexibility of the distal region 228 of catheter 90. That is, by removing the support provided by the core wire 220 in the distal region 228, the flexibility of the distal region 228 may increase. This may allow the distal region 228 to navigate more tortuous paths and reach more distal sites, particularly in a single operator exchange type catheter. Before the radiation delivery tube 20 is advanced into the catheter distal region 228, however, the core wire 220 is moved distally to the distal position and into the centering cone 224. As indicated above, the centering cone 224 may help center the distal end of core wire 220 relative to inner tube 94.

When the core wire 220 is in the distal position, the radiation delivery lumen 98 in combination with core wire 220 may provide a structure that can be used to rapidly advance the radiation source to the lesion site. Further, by sliding the core wire 220 into the distal position, abutting the end of the lumen, it is guaranteed that there is a navigatable path for the radiation source to the site of treatment. This is, there are no kinks that would stop the source from reaching the site. In addition, the core wire 220 may help constrain lateral movement of the radiation delivery tube 20 and help center the radiation delivery tube 20 within the vessel. This may be important to provide a more even radiation exposure to the vessel walls.

Referring now to FIG. 17, a preferred core wire 220 is disclosed. The core wire of FIG. 17 includes a proximal portion 250 having an outside diameter of approximately 0.12 inches. The outside diameter then tapers in a tapered region 252 over a length of approximately 2 inches. A distal section 253 of reduced diameter extends therefrom. In preferred embodiments, the reduced diameter portion ranges from about 0.007 inches about 0.01 inches. A bulbous distal tip 254 is formed on the distal end of the core 220. In a preferred embodiment, the distal tip 254 is a weld ball formed using a coil of platinum wire having a 0.003 inch diameter. The coil is four times wound over a mandrel to form the outside diameter of the ball which is preferably selected to correspond to the outside diameter of the radiation delivery tube. The bulbous tip is preferably radiopaque and provides a fluoroscopically visible point at the site of treatment. This assures that the radiation source is placed properly. Further, the bulbous tip is preferably selected to correspond to the outside diameter of the radiation delivery tube so that if a radiation tube breaks along its length, it can readily be retracted by removing the core wire with the bulbous tip compacting the distal end of the tube to help pull it out proximally.

It is contemplated that the core wire in all of the above-described embodiments may be constructed with a slidably disposed core wire. This may impart greater flexibility to the distal end of the catheter when the core wire is withdrawn to a proximal position, while still providing support to the radiation delivery tube 20 when the core wire 220 is advanced to a distal position.

A preferred method of utilizing embodiments with a slidable or removable core wire includes first placing a guide wire within the vessel lumen across the site to be treated. This is followed by the use of a conventional balloon dilatation catheter to predilate the stenosed area. The conventional balloon catheter is then removed with the guide wire being left in place across the lesion. A centering balloon catheter as disclosed herein, capable of utilizing a radiation source, particularly, one as disclosed in FIG. 8, is then advanced over the guide wire so that the centering balloon is across the cite to be treated. The core wire is then advanced to its distal position so that the bulbous tip is abutting the distal end of the lumen. The proximal end of the core wire is then inserted into the radiation shield so that the radiation tube may be loaded over the core wire. The radiation tube is then advanced to the site over the core wire. Then the guide wire is preferably pulled back proximally so that it does not interfere with exposing the vessel wall to radiation. After a prescribed treatment time, the radiation tube is removed. Following treatment, the catheter and core wire are also remote, preferably together.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter system for inhibiting restenosis comprising:
   an elongate tubular shaft having a lumen, a proximal region and a distal region;
   an inflatable balloon disposed proximate said shaft distal region;
   a radiation source guide wire slidably disposed within said shaft lumen; and
   an elongate radiation delivery tube having a lumen and a distal radioactive region, said delivery tube being slidably disposed about said radiation source guide wire, and slidably disposed in said shaft lumen.

2. A radiation source as recited in claim 1 wherein said radiation delivery tube has tube walls and said radiation delivery tube distal radioactive region includes radioactive material incorporated in said tube walls.

3. A radiation source as recited in claim 1 wherein said radiation delivery tube has a surface and said radiation delivery tube distal radioactive region includes radioactive material secured to said distal region surface.

4. A radiation source as recited in claim 1 wherein said radiation delivery tube has an exterior surface and said radiation delivery tube distal radioactive region includes radioactive wire wound about said distal region exterior surface.

5. A radiation source as recited in claim 1 wherein said radiation delivery tube is formed of metal and said radiation delivery tube distal radioactive region is formed of radioactive metal.

6. A catheter system as recited in claim 1 wherein said radiation delivery tube is formed from Nitinol.

7. A catheter system as recited in claim 1 wherein said radiation delivery tube is a polymeric tube formed from polyethylene.

8. A radiation source as recited in claim 1 wherein said radiation delivery tube has a tube wall and a longitudinal slot through said tube wall, such that the radiation source guide wire can be slid through said longitudinal slot.

9. A radiation source as recited in claim 8 wherein said slot does not extend through at least a portion of said radiation delivery tube distal region.

10. A radiation source as recited in claim 1 wherein said radiation delivery tube distal region has a proximal guide wire port.

11. A catheter system as recited in claim 1 wherein said balloon includes a plurality of lobes.

12. A catheter system as recited in claim 1 wherein said balloon includes a plurality of tubular balloons disposed transversely about said radiation source guide wire.

13. A catheter system for inhibiting restenosis comprising:

an elongate outer tube having a lumen, a proximal region and a distal region;

an inflatable balloon disposed proximate said outer tube distal region;

an elongate inner tube having a lumen, a proximal port, a distal region, and a closed distal end, said inner tube being disposed within said outer tube, said inner tube distal region being disposed inside said balloon;

an inflation lumen defined between said inner and outer tubes, said inflation lumen being in fluid communication with said balloon;

a radiation source guide wire slidably disposed within said inner tube lumen; and an elongate radiation delivery tube having a lumen and a distal radioactive region, said delivery tube being slidably disposed about said radiation source guide wire and slidably disposed in said inner tube lumen.

14. A catheter system for inhibiting restenosis comprising:

a proximal elongate tube having a lumen, a proximal region and a distal skived region;

a distal elongate tube having a lumen, a proximal region and a distal region, wherein the proximal region of said distal elongate tube is operably attached to the distal skived region at a juncture;

an inflatable balloon disposed about said distal elongate tube, said balloon defining a balloon interior and exterior, said balloon interior being sealed with respect to fluid communication with said balloon exterior;

an inflation tubular member having an inflation lumen, a proximal end and a distal end, the proximal end of said inflation tube is in fluid communication with the lumen of the proximal elongate tube, and the distal end of said inflation tube is in fluid communication with the interior of the balloon;

an elongate inner tube having a lumen, a proximal port, a distal region, and a closed distal end, said inner tube extending from the proximal elongate tube, across the juncture and into the interior of the balloon;

a guide wire lumen extending from a proximal port located proximal of the balloon to a distal port located distal of the balloon for slidably receiving a guide wire, said guide wire lumen positioned within at least a portion of the lumen defined by the distal elongate tube;

a radiation source guide wire disposed within said elongate inner tube lumen; and an elongate radiation delivery tube having a lumen and a distal radioactive region, said delivery tube being slidably disposed about said radiation source guide wire, and slidably disposed in said inner tube lumen.

15. A catheter system according to claim 14 wherein said radiation source guide wire is slidably disposed within said elongate inner tube lumen.

16. A catheter system according to claim 14 wherein said radiation source guide wire is fixed relative to said elongate inner tube lumen.

17. A method for inhibiting restenosis comprising:

providing a radiation delivery catheter including an elongate tubular shaft having a lumen, a proximal region and a distal region, an inflatable balloon disposed proximate said shaft distal region;

a radiation source guide wire slidably disposed in said shaft lumen and selectively extending through said shaft lumen and into said balloon;

providing an elongate radiation delivery tube having a lumen and a distal radioactive region, said delivery tube being slidably disposed about said radiation source guide wire, and slidably disposed in said shaft lumen;

inserting said catheter distal region into the vascular system of a patient;

withdrawing said radiation source guide wire proximally of said balloon;

advancing said catheter distal region to a site to be treated;

inflating said balloon;

advancing said radiation source guide wire distally into said balloon;

inserting said radiation source guide wire into said radiation delivery tube lumen;

advancing said radiation delivery tube over said radiation source guide wire and within said tubular shaft lumen;

further advancing said radiation delivery tube within said balloon;

exposing said treatment site to radiation;

deflating said balloon; and retracting said catheter and radiation delivery tube from said patient.

18. A method for inhibiting restenosis as recited in claim 17 further comprising the steps of:

providing a radiation shielding vault having a channel therethrough;

housing said radiation delivery tube distal region in said vault channel prior to use; and advancing said radiation delivery tube distal region into said catheter lumen.

* * * * *